US012692475B2

(12) United States Patent
Kim et al.

(10) Patent No.: US 12,692,475 B2
(45) Date of Patent: Jul. 28, 2026

(54) MICROCARRIER FOR CELL CULTURE AND METHOD FOR PREPARING THE SAME

(71) Applicant: LG CHEM, LTD., Seoul (KR)

(72) Inventors: Minchae Kim, Daejeon (KR); Yeji Kim, Daejeon (KR); Jee Seon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 871 days.

(21) Appl. No.: 17/788,838

(22) PCT Filed: Sep. 10, 2021

(86) PCT No.: PCT/KR2021/012358

§ 371 (c)(1),
(2) Date: Jun. 24, 2022

(87) PCT Pub. No.: WO2022/060015

PCT Pub. Date: Mar. 24, 2022

(65) Prior Publication Data

US 2023/0034857 A1 Feb. 2, 2023

(30) Foreign Application Priority Data

Sep. 15, 2020 (KR) ........................ 10-2020-0118532
Sep. 9, 2021 (KR) ........................ 10-2021-0120325

(51) Int. Cl.
*C12N 5/00* (2006.01)
(52) U.S. Cl.
CPC ........ *C12N 5/0075* (2013.01); *C12N 2533/20* (2013.01)

(58) Field of Classification Search
CPC .............. C12N 5/0075; C12N 2533/20; C12N 2537/10; C08F 212/08; C08F 2/24; C12M 47/04
See application file for complete search history.

(56) References Cited

U.S. PATENT DOCUMENTS 4,994,388 A 2/1991 Hillegas et al.
5,863,957 A * 1/1999 Li ............................. C08F 8/30
521/64

(Continued)

FOREIGN PATENT DOCUMENTS

CA 2886190 A1 9/2016
CN 1903890 A 1/2007

(Continued)

OTHER PUBLICATIONS

Galia, Journal of Polymer Science Part A: Polymer Chemistry, vol. 32, Issue 11, Aug. 1994, p. 2169-2175 (Year: 1994).*

(Continued)

*Primary Examiner* — Robert C Boyle
(74) *Attorney, Agent, or Firm* — ROTHWELL, FIGG, ERNST & MANBECK, P.C.

(57) ABSTRACT

The present application relates to microcarrier particles for cell culture, a method for preparing the particles, and a cell culture medium composition including the particles. According to the present application, a microcarrier having a high degree of uniformity in shape or form, having porosity, and advantageous for cell attachment and isolation of cultured cells is provided.

15 Claims, 3 Drawing Sheets

Example 1

(56) References Cited

U.S. PATENT DOCUMENTS

| | | | |
|---|---|---|---|
| 6,197,285 | B1 | 3/2001 | Kowalik et al. |
| 6,447,791 | B2 | 9/2002 | Kowalik et al. |
| 7,122,582 | B2 | 10/2006 | Konishi et al. |
| 7,129,082 | B2 | 10/2006 | Van Der Merwe et al. |
| 7,910,679 | B2 | 3/2011 | Kiss et al. |
| 8,652,734 | B2 | 2/2014 | Cardoso et al. |
| 2002/0155594 | A1 | 10/2002 | Hsieh et al. |
| 2004/0248291 | A1 | 12/2004 | Yamamoto et al. |
| 2005/0220752 | A1* | 10/2005 | Charmot .............. A61K 9/5031 |
| | | | 424/78.1 |
| 2005/0266244 | A1 | 12/2005 | Park |
| 2005/0272890 | A1 | 12/2005 | Konishi et al. |
| 2007/0202594 | A1* | 8/2007 | Yamamoto ........... C12N 5/0075 |
| | | | 435/325 |
| 2008/0166328 | A1 | 7/2008 | Harmon et al. |
| 2009/0291294 | A1 | 11/2009 | Mori et al. |
| 2010/0093053 | A1 | 4/2010 | Oh et al. |
| 2010/0104527 | A1* | 4/2010 | Mansky ................. A61K 31/78 |
| | | | 424/78.1 |
| 2010/0304482 | A1 | 12/2010 | Deshayes et al. |
| 2010/0317113 | A1 | 12/2010 | Deshayes et al. |
| 2011/0014693 | A1 | 1/2011 | Oh et al. |
| 2011/0111498 | A1 | 5/2011 | Oh et al. |
| 2011/0129919 | A1 | 6/2011 | Oh et al. |
| 2011/0143433 | A1 | 6/2011 | Oh et al. |
| 2011/0294210 | A1 | 12/2011 | Oh et al. |
| 2012/0028352 | A1 | 2/2012 | Oh et al. |
| 2012/0052579 | A1 | 3/2012 | Shannon et al. |
| 2012/0219531 | A1 | 8/2012 | Oh et al. |
| 2012/0309053 | A1 | 12/2012 | Wellings |
| 2014/0193903 | A1 | 7/2014 | Oh et al. |
| 2014/0315300 | A1 | 10/2014 | Oh et al. |
| 2015/0209296 | A1* | 7/2015 | Yamamoto ........... A61K 9/1611 |
| | | | 424/490 |
| 2016/0083690 | A1 | 3/2016 | Birch et al. |
| 2016/0145600 | A1 | 5/2016 | Caracci et al. |
| 2017/0081638 | A1 | 3/2017 | Ma |
| 2018/0201898 | A1 | 7/2018 | Takahashi et al. |
| 2018/0243718 | A1 | 8/2018 | Goldstein et al. |
| 2019/0112572 | A1 | 4/2019 | Figueroa et al. |
| 2019/0144820 | A1 | 5/2019 | Oh et al. |
| 2020/0030786 | A1 | 1/2020 | Raymond |
| 2020/0032122 | A1 | 1/2020 | Nishiumi |
| 2021/0179576 | A1 | 6/2021 | Michaud et al. |
| 2022/0081684 | A1 | 3/2022 | Kim et al. |
| 2023/0250391 | A1 | 8/2023 | Kim et al. |

FOREIGN PATENT DOCUMENTS

| | | | |
|---|---|---|---|
| CN | 101880348 | A | 11/2010 |
| CN | 102327761 | A | 1/2012 |
| CN | 104558350 | A | 4/2015 |
| CN | 206553537 | U | 10/2017 |
| CN | 106226279 | B | 11/2019 |
| CN | 106938861 | B | 7/2020 |
| EP | 4177281 | A1 | 5/2023 |
| JP | H02-16972 | A | 1/1990 |
| JP | H10-501173 | A | 2/1998 |
| JP | 2002-518570 | A | 6/2002 |
| JP | 2002-524489 | A | 8/2002 |
| JP | 2002-306155 | A | 10/2002 |
| JP | 2004-236553 | A | 8/2004 |
| JP | 2004-313008 | A | 11/2004 |
| JP | 2006-136212 | A | 6/2006 |
| JP | 2007-124985 | A | 5/2007 |
| JP | 2007-197471 | A | 8/2007 |
| JP | 2007-275056 | A | 10/2007 |
| JP | 2008-074979 | A | 4/2008 |
| JP | 2010-508851 | A | 3/2010 |
| JP | 2011-514169 | A | 5/2011 |
| JP | 4979946 | B2 | 7/2012 |
| JP | 2012-527901 | A | 11/2012 |
| JP | 2012-242827 | A | 12/2012 |
| JP | 2013-504669 | A | 2/2013 |
| JP | 5636285 | B2 | 12/2014 |
| JP | 2016-521124 | A | 7/2016 |
| JP | 6200621 | B2 | 9/2017 |
| JP | 6416206 | B2 | 10/2018 |
| JP | 2019-510499 | A | 4/2019 |
| JP | 6528508 | B2 | 6/2019 |
| JP | 2020-039356 | A | 3/2020 |
| KR | 10-2001-0053046 | A | 6/2001 |
| KR | 10-0479218 | B1 | 3/2005 |
| KR | 10-0803836 | B1 | 2/2008 |
| KR | 10-0842378 | B1 | 7/2008 |
| KR | 10-0871652 | B1 | 12/2008 |
| KR | 10-2009-0128287 | A | 12/2009 |
| KR | 10-2014-0008383 | A | 1/2014 |
| KR | 10-2014-0056014 | A | 5/2014 |
| KR | 10-1545217 | B1 | 8/2015 |
| KR | 10-2016-0067474 | A | 6/2016 |
| KR | 10-2017-0114993 | A | 10/2017 |
| KR | 10-1975100 | B1 | 10/2017 |
| KR | 10-2017-0121469 | A | 11/2017 |
| KR | 10-2018-0049013 | A | 5/2018 |
| KR | 10-2019-0074125 | A | 6/2019 |
| KR | 10-2019-0138780 | A | 12/2019 |
| KR | 10-2021-0011340 | A | 2/2021 |
| WO | 2012-110443 | A1 | 8/2012 |
| WO | 2015-139462 | A1 | 9/2015 |
| WO | 2019-229384 | A1 | 12/2019 |

OTHER PUBLICATIONS

Supplementary European Search Report for EP 21869602.9 mailed Oct. 17, 2024, 8 pages.

Huang, et al., "Synthesis and Characterization of Crosslinked Porous Poly (styrene-co-divinylbenzene) Microspheres with Tunable Particle and Pore Diameters", Chinese Journal of Applied Chemistry, (2016) vol. 33, Iss. 4, pp. 406-411, with English Abstract, 6 pages.

Costa et al., "Highly Magnetizable Crosslinked Chloromethylated Polystyrene-Based Nanocomposite Beads for Selective Molecular Separation of 4-Aminobenzoic Acid", ACS Omega, 2019, 4, pp. 5640-5649.

Poinescu I.C. et al., "Styrene Divinylbenzene Copolymers", Die Angewandte Makromolekulare Chemie, 1998, vol. 164, pp. 45-58 (Nr. 2659).

Zuidema H: "Ring Method for the Determination of Interfacial Tension", Industrial and Engineering Chemistry, May 1, 1941, vol. 13, No. 5, pp. 312-313.

Extended European Search Report dated Jun. 26, 2023, of the corresponding European Patent Application No. 21869637.5, 14 pages.

International Search Report issued for International Application No. PCT/KR2020/009642 on Nov. 11, 2020, 4 pages.

International Search Report dated Dec. 28, 2021, of the corresponding application PCT/KR2021/012358, 3 pages.

International Search Report issued for International Application No. PCT/KR2021/011985 on Dec. 31, 2021, 4 pages.

Partial supplementary European Search Report dated Feb. 1, 2022, of the corresponding European Patent Application No. 20845090.8, 16 pages.

Tavassoli, et al., "Large-scale production of stem cells utilizing microcarriers: A biomaterials engineering perspective from academic research to commercialized products", Biomaterials (2018)vol. 181, pp. 333-346.

Zhang, et al., "Synthesis of Porous Microparticles with Aligned Porosity" Advanced Functional Materials, (2008) vol. 18, No. 2, pp. 222-228.

Olayo et al., Poly (vinyl alcohol) as a Stabilizer in the Suspension Polymerization of Styrene: The Effect of the Molecular Weight, Journal of Applied Polymer Science 1998, vol. 67, 71-77.

Bolten et al., Experimental Study on the Surface Tension, Density, and Viscosity of Aqueous Poly(vinylpyrrolidone) Solutions, Journal of Chemical & Engineering Data, 2011, 56, 3, 582-588.

Gutsche et al., "N-Acetylglucosamine and Adenosine Derivatized Surfaces for Cell Culture: 3T3 Fibroblast and Chicken Hepatocyte Response," Biotechnology and Bioengineering, vol. 43, pp. 801-809 (1994).

(56) References Cited

OTHER PUBLICATIONS

"Corning polystyrene microcarrier 500 g Synthemax II treated," https://www.ddbiolab.com/article/004623?language=en, accessed Jun. 29, 2024, 1 page.

Lerman et al., "The Evolution of Polystyrene as a Cell Culture Material", Tissue Engineering Part B, vol. 24, No. 5, 2018, pp. 359-372 (14 pages).

Wong, Libretext Biology, Axoloti Academia Publishing, 1.7: Fatty Acids (Year: 2021) 341 pages.

Rafiq et al. "Systematic microcarrier screening and agitated culture conditions improves human mesenchymal stem cell yield in bioreactors." Biotechnology journal (2016): 11, 473-486.

Nazli et al., Under the Microscope: Microcarriers, International Society cell & gene therapy, 2021, 7 pages.

Reibetanz et al., "Magnetite nanoparticles as reporters for microcarrier processing in cytoplasm." Nuclear Instruments and Methods in Physics Research B. (2011): vol. 269, Issue 2, pp. 2281-2285.

Ataman Chemicals, Dodecane, 2020, 7 pages.

Sigman Aldrich, Products: Food & cosmetics component standards: 44010, Dodecane, 2026, 11 pages.

Mindat.org, Magnetite, 2026, 20 pages.

* cited by examiner

FIG 2(a)    Comparative Example 1
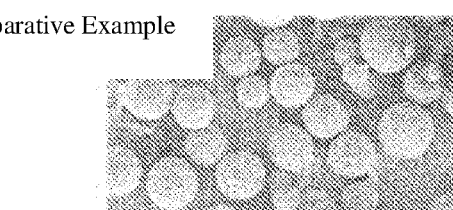
FIG 2(b)    Comparative Example 2
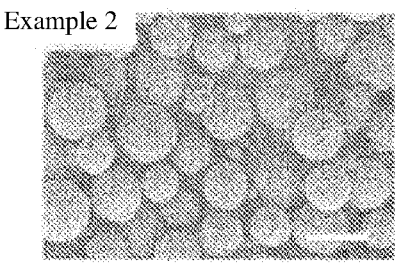
Comparative Example 3
FIG 2(c)
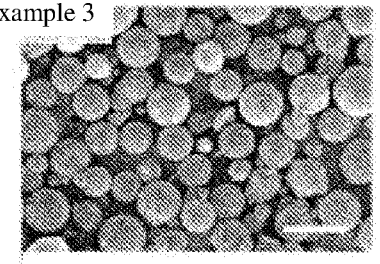
FIG 2(d)    Comparative Example 4
FIG 2(e)    Comparative Example 5
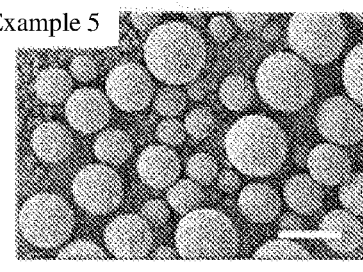

MICROCARRIER FOR CELL CULTURE AND METHOD FOR PREPARING THE SAME

CROSS-REFERENCE TO RELATED APPLICATION(S)

This application is a 35 U.S.C. 371 National Phase Entry Application from PCT/KR2021/012358, filed on Sep. 10, 2021 and designating the United States, which claims the benefit of Korean Patent Application No. 10-2020-0118532 filed Sep. 15, 2020 and Korean Patent Application No. 10-2021-0120325 filed on Sep. 9, 2021 in the Korean Intellectual Property Office, the disclosures of which are incorporated herein by reference in their entirety.

TECHNICAL FIELD

The present application relates to a microcarrier and a method for preparing the same. More particular, the present application relates to a microcarrier that can be used for cell culture and a method for preparing the same.

BACKGROUND OF THE INVENTION

Along with the expansion of the fields of biopharmaceuticals and regenerative medicine, the need for the large-scale culture techniques capable of efficiently preparing cells, tissues, microorganisms, and the like is growing. For example, the technology for culturing cells using microcarriers has been actively developed.

In microcarrier-related cell culture techniques, adherent cells are cultured using a microcarrier within a 3D bioreactor. Specifically, a cell, a culture medium, and a microcarrier are put in a bioreactor, and the cell are brought into contact with the microcarrier while stirring the culture medium, so that the cells are attached to the microcarrier surface to culture. The microcarrier used at this time should have a high surface area/volume to which cells can attach and grow, so as to be suitable for the large-scale culture of cells.

Meanwhile, currently commercially used microcarriers have a size of 100 to 300 μm and a density of about 1.1 to 1.3 g/cm³. And, the density of cells cultured after adhering to the carriers is about 1.2 g/cm³. Due to the density of these carriers and cells, it is advantageous to adhere cells to carriers at early stages of culturing the cells within the bioreactor, but at the time of isolating and recovering cells after culturing, application of a centrifugal separation is difficult. Therefore, in addition to the centrifugal separation, a separate filtering method capable of isolating and recovering cells based on the size of microcarriers and cell should be utilized. However, the filtering method based on the carrier size and cell size shows problems that as the process is repeated, the filter is clogged, the process time is long, the physical damage and contamination of cells are occurred, which may lead to loss of cells during the filtering process. In order to solve the above problems, it may be considered that microcarriers were prepared using the properties of materials (polymers or polymerizable components forming the skeleton of microcarriers) having a density of less than 1.0 g/cm³ or more than 1.3 g/cm³. However, in such a case, the density range of the carriers that can be implemented is limited, so the adhesion between the microcarrier and the cell is not sufficient, and the culture efficiency is also poor. For example, at the time of stirring a culture medium containing carriers and cells, if the density of the carriers is too low, most of the carriers floats on the surface of the culture medium independently of stirring, and if the density of the carriers is too high, most of the carriers sinks to the bottom of the culture medium independently of stirring. Consequently, cell adhesion to the carriers is poor, and the culture efficiency is reduced.

Therefore, there is a need to develop a microcarrier-related technique that can be uniformly dispersed in the culture medium, which is advantageous for cell adhesion and culture, and facilitates isolation and recovery of cells after culturing.

BRIEF SUMMARY OF THE INVENTION

An object of the present application is to provide a microcarrier used for cell culture.

Another object of the present application is to provide a microcarrier having a high degree of uniformity in shape or form.

Another object of the present application is to provide porous microcarrier particles having the properties described below.

Yet another object of the present application is to provide a microcarrier that is advantageous for cell adhesion and culture, and can more easily isolate microcarriers and cells after culturing.

Still yet another object of the present application is to provide a composition comprising cells and the microcarrier.

The above and other objects of the present application can be entirely achieved by the present application described in detail below.

DETAILED DESCRIPTION OF THE INVENTION

In one embodiment, the present application relates to a method for preparing porous microcarrier particles. The above method may include the step of mixing a continuous phase composition (A) and a dispersive phase composition (B) and performing suspension polymerization.

As used herein, the term "microcarrier particles" means particles having a micro-level size (diameter), a particle group containing such particles, or a particle group consisting of such particles. For example, according to the present application, a particle group containing individual particles having the longest dimension length in the range of 50 to 400 μm in their shape can be provided. The size can be measured by the same method as described below. If the particle diameter is less than 50 μm, the surface area for cell culture is small and thus, the culture efficiency may be lowered. In addition, when the particle diameter exceeds 400 μm, the density of adhered cells is low, and an interaction between adhered cells is not sufficient, and thus, the culture efficiency may be reduced.

As used herein, the term "porosity" may mean the properties of particles at least having voids therein.

As used herein, the term "dispersive phase composition" means a composition capable of forming a dispersive phase (or droplet) after being mixed with a continuous phase composition.

As used herein, the term "continuous phase composition" means a composition capable of forming a continuous phase after being mixed with a dispersive phase composition.

In the present application, unless otherwise defined or described, the temperature at which the preparation process is performed (or each preparation step) or the temperature at which the numerical properties processed by the prepared particles are calculated or measured may be a normal temperature (or room temperature). Specifically, in the present application, the "normal temperature" is a temperature in a state where the temperature is not particularly raised or reduced, which may mean, for example, a temperature in the range of 15 to 30° C.

The present inventors have found through experiments that when a continuous phase (composition) satisfying a predetermined condition is used for preparing microcarrier particles, it has high shape uniformity and size uniformity, has lower density properties than normally cultured cells, is excellent in surface flatness and can ensure porous carrier particles with a high recovery rate.

Below, the preparation method of the present application will be described in detail.

A preparation method according to the present application includes the steps of mixing a continuous phase composition (A) simultaneously satisfying the following conditions 1 and 2; and a dispersive phase composition (B) containing a polymerizable monomer (b1) and then performing suspension polymerization. At this time, the suspension polymerization may be performed at the interface between the formed continuous phase and dispersive phase (that is, the surface of the dispersive phase droplet) and/or inside the dispersive phase after mixing the dispersive phase composition and the continuous phase composition.

$$45 \text{ mN/m} < \text{Surface Tension of Continuous Phase Composition} \leq 54 \text{ mN/m} \qquad \text{[Condition 1]}$$

$$\text{Viscosity of Continuous Phase Composition} \geq 2.0 \text{ cp} \qquad \text{[Condition 2]}$$

According to specific embodiments of the present application, the surface tension related to the condition 1 can be measured at normal temperature according to a ring method.

According to specific embodiments of the present application, the viscosity related to the condition 2 can be measured according to a shear rate. Specifically, the viscosity can be measured under the conditions of a shear rate in the range of 66 to 264 l/s and normal temperature. The upper limit of the viscosity of the continuous phase composition may be, for example, 5.0 cp or less, 4.5 cp or less, 4.0 cp or less, 3.5 cp or less, 3.0 cp or less, or 2.5 cp or less, although not being especially limited thereto.

When both condition 1 and condition 2 are simultaneously satisfied, particles suitable for the purposes of the present application described below can be provided in high yield.

In one embodiment, the continuous phase composition (A) may include water and poly(vinyl alcohol) (PVA). Although not particularly limited, water may be distilled water or deionized water.

In one embodiment, the continuous phase composition (A) may be a mixture of water and polyvinyl alcohol. That is, the continuous phase composition (A) may consist of only water and polyvinyl alcohol.

In one embodiment, the polyvinyl alcohol (PVA) may have an average weight molecular weight (MW) in a predetermined range and a hydrolyzed degree in a predetermined range. Specifically, the weight average molecular weight of polyvinyl alcohol may be in the range of 80,000 to 190,000. More specifically, the lower limit of the weight average molecular weight may be, for example, 85,000 or more, and the upper limit may be, for example, 180,000 or less, 175,000 or less, 170,000 or less, 165,000 or less, 160,000 or less, 155,000 or less, 150,000 or less, 145,000 or less, 140,000 or less, 135,000 or less, 130,000 or less, or 125,000 or less. And, the hydrolyzed degree of the polyvinyl alcohol may be in the range of 80 to 99%. More specifically, the lower limit of the hydrolyzed degree may be, for example, 81% or more, 82% or more, 83% or more, 84% or more, or 85% or more, and the upper limit may be, for example, 98% or less, 97% or less, 96% or less, 95% or less, 94% or less, 93% or less, 92% or less, 91% or less, or 90% or less. The weight average molecular weight can be measured using GPC, and the hydrolyzed degree can be measured using 1H-NMR.

Polyvinyl alcohol, which satisfies the molecular weight and the hydrolyzed degree, enables the continuous phase composition (A) to satisfy the condition 1 and the condition 2. Specifically, when the weight average molecular weight of PVA satisfies the above range, the length of the polymer chain increases, and the entanglement and aggregation of the molecular chains also increase at an appropriate level, which is advantageous for ensuring the viscosity of the continuous phase (condition 2). In addition, when the PVA satisfies the weight average molecular weight in the above range, it is considered that the intermolecular force increases and the surface tension increases, which is advantageous for ensuring the above-mentioned surface tension of the continuous phase (condition 1). Further, the hydrolyzed degree (or saponification degree) affects the solubility and hydrophilicity (or hydrophobicity) in water. It is considered that PVA, satisfying the weight average molecular weight and the hydrolyzed degree, acts advantageously for ensuring the condition 1 and the condition 2, and stably forming the dispersive phase.

In one embodiment, in the continuous phase composition (A), the concentration of polyvinyl alcohol may be 1.0% or more. For example, when a continuous phase composition, which is a mixture of water and polyvinyl alcohol, is used, the content of polyvinyl alcohol may be 1.0% by weight or more based on the total weight (100% by weight) of the continuous phase composition. Although not particularly limited, the upper limit of the polyvinyl alcohol concentration may be, for example, less than 5.0%, more specifically 4.5% or less, 4.0% or less, 3.5% or less, 3.0% or less, 2.5% or less, or 2.0% or less. When polyvinyl alcohol satisfying the above range is used, it is advantageous to obtain a continuous phase composition that simultaneously satisfies the condition 1 and the condition 2.

In one embodiment, the polymerizable monomer (b1) contained in the dispersive phase composition (B) may be a styrene monomer. The styrene monomer can be subjected to suspension polymerization to produce polystyrene or a polystyrene-based polymer. That is, the carrier particles prepared according to the method of the present application may be polystyrene particles or polystyrene-based particles.

In one embodiment, the styrene (b1) may be contained in the dispersive phase in only remaining amounts, excluding the total content of the other components (e.g., oil, initiator, and/or crosslinking agent) of the dispersive phase composition described below, among the total content (100% by weight) of the dispersive phase composition. For example, the dispersive phase composition may include the styrene (b1) in an amount of 60% by weight or more, 65% by weight or more, 70% by weight or more, or 75% by weight or more, based on the total content (100% by weight) of the dispersive phase composition content. And, the upper limit of the content of the styrene (b1) may be, for example, less than 90% by weight, 85% by weight or less, or 80% by weight or less.

In one embodiment, the dispersive phase composition (B) may further include a crosslinking agent in addition to the styrene monomer. When only styrene monomer is used as a polymerization component, the crosslinking density of the polystyrene polymer forming the particles is reduced, which may make it difficult for the carrier particles to maintain a spherical shape. When the prepared particles have a spherical shape, a large surface area can be secured, and the cell adhesion performance to the carrier is high compared to the non-spherical shape. As the crosslinking agent, for example, an ethylenically unsaturated crosslinking agent (b2) containing a vinyl functional group can be used.

In one embodiment, the ethylenically unsaturated crosslinking agent (b2) may include divinylbenzene, N-vinyl pyrrolidone, N,N-dimethyl acrylamide, (meth)acrylic acid, acrylamide, N-octyl acrylamide, vinyl acetate, and mixtures of two or more thereof. Considering the density of the prepared carriers, the cell culture process, and the like, it may be preferable to use divinylbenzene as the ethylenically unsaturated crosslinking agent.

In one embodiment, the dispersive phase composition (B) may contain 3 to 300 parts by weight of an ethylenically unsaturated crosslinking agent based on 100 parts by weight of the styrene monomer. When the content of the ethylenically unsaturated crosslinking agent is less than 3 parts by weight, the crosslinking density of the styrene particles is excessively reduced, which makes it difficult for the form of the particles to maintain a stable spherical shape. In addition, when the content exceeds 300 parts by weight, the crosslinking density is excessively increased, which makes it difficult to secure the density level of particles suitable for cell culture and centrifugal separation.

In one embodiment, the content of the styrene monomer in the dispersive phase composition may be excessive relative to the content of the ethylenically unsaturated crosslinking agent. For example, based on 100 parts by weight of the styrene monomer, the ethylenically unsaturated crosslinking agent may be used in an amount of 80 parts by weight or less, 70 parts by weight or less, 60 parts by weight or less, 50 parts by weight or less, or 40 parts by weight or less. In this case, the lower limit of the content of the ethylenically unsaturated crosslinking agent may be, for example, 3 parts by weight or more, and specifically, for example, it may be 5 parts by weight or more, 10 parts by weight or more, 15 parts by weight or more, 20 parts by weight or more, or 25 parts by weight or more.

In one embodiment, the dispersive phase composition (B) may include a hydrocarbon oil (b3). In a conventional technique, foamed styrene particles were prepared using a foaming agent in an attempt to reduce the density of microcarrier particles, but when using a foaming agent, the distribution range of particle diameter and density becomes excessively wide, and thus, it was not easy to obtain carrier particles having a diameter and density suitable for cell culture applications in sufficient yield. However, in the present application using the hydrocarbon oil (b3) in the dispersive phase composition (B), there is no need to perform a foaming process in connection with lowering the density of the carrier particles. That is, the particles of the present application are non-foamed particles.

Specifically, the hydrocarbon oil may come out of the dispersive phase during suspension polymerization process performed while stirring a mixture of the dispersive phase and the continuous phase. As a result, the microcarrier particles can have porosity and at the same time have low density properties. Moreover, even if hydrocarbon oil remains in the dispersive phase during suspension polymerization, the hydrocarbon oil has a low density as described below and does not participate in suspension polymerization, and therefore, the density of the microparticles may be reduced. That is, the present application, which is performed without foaming treatment, can more precisely adjust the diameter and density distribution range of the carrier particles. Furthermore, according to specific embodiments of the present application, the low-density carrier particles obtained using the hydrocarbon oil do not sink to the bottom of the culture medium nor float on the surface of the culture medium, and can be maintained in a state of being uniformly dispersed in the culture medium. As a result, the particles of the present application can improve the floating degree of carrier particles in the culture medium, thereby increasing the adhesion between the carrier particles and cells, and increasing the culture efficiency.

The type of the hydrocarbon oil that can be used for the dispersive phase is not particularly limited, but may be selected in consideration of the easiness of performing the preparation method or the assurance of the properties of carrier particles described hereinafter. For example, a low-density hydrocarbon oil having an upper limit of density of $0.800$ g/cm$^3$ or less or $0.790$ g/cm$^3$ or less can be used. At this time, the lower limit of the density of the low-density hydrocarbon oil is not particularly limited, but may be, for example, $0.750$ g/cm$^3$ or more or $0.760$ g/cm$^3$ or more.

In one embodiment, the hydrocarbon oil may include one or more linear or branched saturated hydrocarbon compounds having 12 or more and 50 or less carbon atoms. Specifically, the hydrocarbon oil may include, for example, a normal alkane having 12 to 16 carbon atoms, an isoalkane having 12 to 16 carbon atoms, or a mixture thereof. According to specific embodiments of the present application, dodecane having 12 carbon atoms, hexadecane having 16 carbon atoms, or Isopar M (a mixture of an isoalkane having 12 or more and 14 or less carbon atoms and an isoalkane having 13 or more and 16 or less carbon atoms) can be used as the hydrocarbon oil.

In one embodiment, the dispersive phase composition (B) may contain 10 to 30% by weight of the hydrocarbon oil based on the total weight (100% by weight) of the dispersive phase composition. Specifically, the lower limit of the content of the hydrocarbon oil may be 11% by weight or more, 12% by weight or more, 13% by weight or more, 14% by weight or more, or 15% by weight or more, and the upper limit may be, for example, 25% by weight or less or 20% by weight or less. By using the oil in the above content range, the effect due to the use of the oil can be secured, such as obtaining particles of a density suitable for cell culture and centrifugal separation. For example, if the hydrocarbon oil is used below the content range, it is difficult to ensure carrier particles having low-density properties, and if the hydrocarbon oil is used beyond the above content range, it becomes difficult to obtain spherical particles, and the uniformity of the particle shape is poor.

In one embodiment, the dispersive phase composition (B) may further include an initiator (b4). The type of the initiator is not particularly limited as long as it does not interfere with the assurance of particle properties in accordance with the preparation method of the present application. For example, an initiator such as an organic peroxide initiator or an azo group initiator can be used. Specifically, compounds such as benzoyl peroxide, di-t-amyl peroxide, t-butyl peroxybenzoate, 2,5-dimethyl-2,5 di-(t-butylperoxy) hexane, 2,5-dimethyl-2,5-di-(t-butylperoxy) hexyne-3 or di-cumyl peroxide, and mixtures thereof can be used, but the present application is not limited thereto.

The content of the initiator is not particularly limited. The initiator can be used in appropriate amounts at levels that do not interfere with the assurance of the desired properties of the particles. For example, the dispersive phase composition (B) can contain the initiator in an amount in the range of 0.10 to 5.00% by weight, 0.50 to 4.00% by weight, or 1.00 to 3.00% by weight, based on the total weight (100% by weight) of the dispersive phase composition.

In one embodiment, the styrene and the crosslinking agent can be contained in the dispersive phase composition in only remaining amounts, excluding the total content of the above-mentioned other components (e.g., oil, initiator, etc.), among the total content (100% by weight) of the dispersive phase composition. For example, based on the total content (100% by weight) of the dispersive phase composition, the total content of the styrene (b1) and the crosslinking agent may be 60% by weight or more, 65% by weight or more, 70% by weight or more, or 75% by weight or more, and the upper limit of the total content may be, for example, less than 90% by weight, 85% by weight or less, or 80% by weight or less. In such a case, the relative content ratio between the styrene and the crosslinking agent may satisfy the range of the above-mentioned ratio (styrene monomer:ethylenically unsaturated crosslinking agent=100 parts by weight: 3 to 300 parts by weight).

The content of the continuous phase composition (A) and the dispersive phase composition (B) is suitable for forming droplets of a uniform dispersive phase and performing suspension polymerization, and can be adjusted at a level that does not interfere with the assurance of the properties of the particles described below. For example, the ratio ($W_B$/$W_A$) between the weight of the continuous phase composition ($W_A$) and the weight of the dispersive phase composition ($W_B$) may be in the range of 0.05 to 0.30. More specifically, the ratio may be in the range of 0.10 to 0.25.

The suspension polymerization may be performed under conditions that do not interfere with the assurance of particle properties according to the preparation method of the present application. For example, the suspension polymerization may be performed under the conditions of a temperature of 80 to 95° C. and a speed of 300 to 900 rpm.

In one embodiment, the suspension polymerization can be performed under nitrogen purging conditions.

The time during which suspension polymerization is performed is not particularly limited. For example, the suspension polymerization can be performed for several hours, specifically about 3 to 10 hours.

In one embodiment, the method may include a step of mixing the continuous phase composition (A) and the dispersive phase composition (B) and then applying a shearing force to homogenize the dispersive phase composition (B) in the form of droplets in the continuous phase composition (A); and a step of subjecting the dispersive phase composition to suspension polymerization. The details concerning the suspension polymerization are the same as those described above.

The step of homogenizing the dispersive phase composition (B) in the form of droplets can be performed through stirring at normal temperature. The stirring speed performed at normal temperature is not particularly limited, but for example, it can be in the range of 300 rpm to 900 rpm.

In one embodiment, the method may further include a step of additionally adding the continuous phase composition (A) during progress of suspension polymerization. Specifically, a mixture of polyvinyl alcohol and water can be additionally added during suspension polymerization. In this regard, "during progress of suspension polymerization" may mean after the above-mentioned suspension polymerization conditions (temperature and speed) have been formed, or alternatively, it may mean a time point when the polymerization rate related to suspension polymerization is in the range of at least 5% to 70%. When polyvinyl alcohol is additionally added, it was confirmed that the flatness of the prepared particles is improved, and the proportion of single-shaped particles among the total prepared particles is increased (see the contents related to Example 3 in Table 1 and Table 2). By "the flatness is improved" is meant herein less defects on the particle surface caused by particle aggregation and separation. This is considered to be because the aggregation between particles is suppressed by the continuous phase composition that is additionally added during the dispersion phase-related suspension polymerization. Components constituting the additionally added continuous phase composition (A) and the other properties are the same as those described above.

In another embodiment, the method may further include a step of forming a primer layer and/or a cell adhesion-inducing layer on the surface of the suspension polymerization reaction product (carrier particles) after completion of the suspension polymerization reaction.

The primer layer enables the introduction of a functional polymer to the surface of the microcarrier particle having no functional group, and serves as a so-called adhesive layer. For example, the cell adhesion-inducing layer or cells can be stably maintained on the particles via the primer layer.

Although not particularly limited, as the compound capable of forming the primer layer, a catechol derivative capable of inducing water-phase adhesion can be used. For example, any one or more selected from the group consisting of L-dihydroxyphenylalanine (L-DOPA), dopamine, norepinephrine, epinephrine, epigallocatechin and derivatives thereof can be used in the formation of the primer layer. The primer layer formed by containing the compound can impart hydrophilicity to the particle surface to further enhance the dispersibility of the particles within the aqueous dispersion which is a continuous phase.

In one embodiment, the ratio of the radius of the polystyrene-based particles to the thickness between the primer layers may be 1:0.00001 to 1:0.01, or 1:0.0001 to 1:0.001. When the ratio of the radius of the polystyrene-based particles to the thickness of the surface coating layer is too low, the primer layer is too thin compared to the polystyrene-based particles, and the effect of modifying the surface of the microcarrier to be hydrophilic is insignificant. When the primer layer is too high, the primer layer becomes thicker compared to the polystyrene-based particles, and the adhesion efficiency between cells and microcarriers during cell culture may be reduced.

The cell adhesion-inducing layer is composed of cell adhesion substances, which serve to provide attachment sites for cell transmembrane proteins. Thereby, adherent cells can be stably adhered, spread, and cultured. Although not particularly limited, any one or more selected from the group consisting of gelatin, collagen, fibronectin, chitosan, polydopamine, tannic acid, polyphenol, poly L-lysine, vitronectin, RGD-containing peptide, lignin, cationic dextran, and derivatives thereof can be used as the compound for forming the cell adhesion-inducing layer. In addition, the cell adhesion-inducing layer formed by containing the compound can modify the surface of the (polystyrene) particles to be hydrophilic, thereby improving the water dispersibility of the carriers.

In one embodiment, the method may further include a washing step after completion of the suspension polymerization reaction. Impurities irrelevant to carrier particles that are suspension polymerization products can be removed by washing. The washing method is not particularly limited, and a known washing method can be used. For example, the washing may be performed by adding a suspension polymerization product to alcohol such as ethanol and stirring the mixture. Although not particularly limited, such washing can be repeated, for example, three or more times.

In one embodiment, the washing may be performed after forming a primer layer and/or a cell adhesion-inducing layer on the surface of the carrier particles.

In one embodiment, the method may further include a drying step after the washing. Solvent residues and the like can be removed through drying. The drying method is not particularly limited, and a known drying method can be used. For example, the drying can be performed using an oven or under normal temperature conditions. In addition, although not particularly limited, the drying may be performed in a vacuum.

In one embodiment, the method may further include a step of washing and drying the suspension polymerization product after completion of the suspension polymerization reaction. The details concerning the washing and drying are the same as those described above.

Particles prepared according to the method described above can have properties suitable for cell culture.

In one embodiment, the method can provide particles having high shape or form uniformity. Specifically, as confirmed through Examples described below, for the particles prepared according to the method of the present application, at least 80% of the total number of the prepared particles may have a single shape. That is, according to the method, the ratio of single-shaped particles among the whole prepared particles can satisfy 80% or more. Herein, the "single shape" means a particle in which satellite particles do not exist on the surface thereof. Compared to particles having satellite particles on their surface, single-shaped particles can have a larger surface area, which is advantageous for cell adhesion.

In one embodiment, the method can provide spherical particles. The spherical shape generally means that it has a form close to a spherical shape, and can be confirmed with the naked eye, but for example, it may mean the case in which a sphericity value calculated by Equation 1 below is about 0.80 or more. When the particles have a spherical shape, a large surface area can be secured and the cell adhesion performance of the carriers can be improved. In specific embodiments of the present application, the particles prepared according to the present application may have a spherical shape, or at least the single-shaped particles may have a spherical shape.

$$\text{Sphericity} = \frac{\pi^{1/3}(6V_p)^{2/3}}{A_p} \qquad \text{[Equation 1]}$$

(in Equation 1, $V_p$ is the volume of the particle, and Ap is the surface area of the particles.) In one embodiment, the method can provide porous particles having one or more pores with a size of 0.5 μm or more or 1 μm or more formed therein. The pores can be confirmed through particle analysis using a scanning electron microscope (SEM). At this time, the size of the pores may be the longest (virtual) straight line distance connecting both ends of the pores visually confirmed from the cross-section of the particles (e.g., when looking at particles from the outside of the particles). The shape or distribution of the pores may vary depending on the movement of hydrocarbon oil generated during suspension polymerization of the dispersive phase droplets. For example, one or more pores may be present inside the particles in various shapes. The upper limit of the pore size may vary depending on the size of the entire particles, but may be, for example, 5 μm or less, 4.5 μm or less, 4.0 μm or less, 3.5 μm or less, 3.0 μm or less, 2.5 μm or less, or 2.0 μm or less.

In this regard, the porous particles obtained according to specific embodiments of the present application may be particles having a porosity degree or a porosity of about 15.0% or less calculated by Equation 2 below. The lower limit of the porosity of the particles may be, for example, greater than 0%, 1% or more, 2% or more, 3% or more, 4% or more, or 5% or more.

This porosity is related to the density properties of the particles.

$$\text{Porosity} = \{1-(\text{Apparent Density/True Density})\} \times 100 \qquad \text{[Equation 2]}$$

(in Equation 2, the apparent density is the density obtained by using the volume of the particle(s) including a space between particles, and the true density is the density obtained by using the volume of only particles excluding the space. At this time, the true density can be measured with a helium pycnometer (Micromeritics Corp.) equipment, and the apparent density can be measured through an ethanol flotation process as described in Experimental Examples below.

In one embodiment, the method can provide particles having a micrometer level size (in the range of about 50 to 400 μm), specifically particles having a diameter in the range of 90 to 250 μm, more specifically particles having a diameter in the range of 110 to 210 μm. Specifically, the method can provide single-shaped spherical particles having a diameter in the range of 90 to 250 μm. The diameter can be measured using a particle size analyzer (PSA). Alternatively, the two-dimensional (2D) plane area of the particles may be determined through an optical microscope, and the diameter can be calculated by back calculating Equation (S=πr²) for the plane area. At this time, the diameter may be an arithmetic mean of values calculated for at least 100 particles. When the particle diameter is less than the above range, the cell adhesion performance is poor, and when it exceeds the above range, it has the effect of reducing the reference surface area for the same volume, and therefore, similarly, it is difficult to expect excellent cell adhesion performance. According to specific embodiments of the present application, the diameter may be a diameter of a single-shaped particle.

In one embodiment, the method can provide particles having a density in the range of 0.95 g/cm³ to 1.00 g/cm³. A method of confirming the density of the particles is not particularly limited. For example, as described in the Experimental Example below, the density of the particles can be confirmed by a method of charging the particles into a solution having a predetermined density, and then confirming whether the particles floated or settled. Considering that the density of conventional commercial carrier particles used for cell (which have a density of about 1.2 g/cm³ level) culture is about 1.1 to 1.3 g/cm³, the carrier particles prepared according to the present application have low density properties. Therefore, when the cultured cells are isolated and recovered from the microcarrier particles, the difference in sedimentation rate due to gravity may be greater than when using conventional carrier particles, and therefore, the microcarriers and cells can be more easily isolated. In one embodiment, the lower density limit of the microcarrier particles may be 0.95 g/cm³ or greater, and the upper limit may be 0.995 g/cm³ or lower. When the density of the microcarrier particles exceeds 0.995 g/cm³ and approaches 1.00 g/cm³ or becomes larger than that, the difference in density between cells and microcarriers is small, centrifugal separation is difficult when isolating and recovering cells after culturing. In addition, when the density of the microcarrier particles become less than 0.95 g/cm³ and approaches 0.90 g/cm³, it is difficult to attach cells to the microcarrier particles at early stages of culturing the cells, and is unsuitable for culture.

In one embodiment, the method of the present application can provide particles having the above properties with a recovery rate in the range of 70 to 95%. The recovery rate of the particles can be calculated as described in Experimental Examples below.

The carrier particles prepared according to the present application as described above can be used for cell culture.

In another embodiment of the present application, the present application relates to microcarrier particles. The microcarrier particles can be prepared by the method described above.

In one embodiment, the porous microcarrier particles may include polystyrene. That is, the microcarrier particles obtained by suspension polymerization of a styrene monomer may be polystyrene particles or polystyrene-based particles.

In one embodiment, the polystyrene particles or polystyrene-based particles may be a polymerization product of a styrene monomer and an ethylenically unsaturated crosslinking agent. Specifically, the polystyrene may be a suspension polymerization reaction product (poly(styrene-co-divinylbenzene)) of a styrene monomer and a divinylbenzene crosslinking agent.

In one embodiment, the microcarrier particles may further include a primer layer and/or a cell adhesion-inducing layer on their surface. The details concerning this are the same as those described above.

In one embodiment, the microcarrier particles may be particles in which 80% or more of the total particles based on the number satisfy a single shape. The details concerning the single shape are the same as those described above.

In one embodiment, the microcarrier particles may have a spherical shape. The details concerning the spherical shape are the same as those described above.

In one embodiment, the microcarrier particles may be porous. The details concerning porosity and pores are the same as those described above. For example, the microcarrier particles may have a pore size of 5 μm or less. At this time, the pores may be formed inside the particles. According to specific embodiments of the present application, the lower limit of the pore size may be, for example, 0.5 μm or more or 1 μm or more. In addition, the upper limit may be, for example, 4.5 μm or less, 4.0 μm or less, 3.5 μm or less, 3.0 μm or less, 2.5 μm or less, or 2.0 μm or less.

In one embodiment, the microcarrier particles may have a diameter in the range of 90 to 250 μm. Specifically, the diameter of the particles having a single shape among the microcarrier particles may satisfy the range of 90 to 250 μm. The details concerning the carrier particle diameters are the same as those described above.

In one embodiment, the microcarrier particles may have a density in the range of 0.95 g/cm³ to 1.00 g/cm³. The details concerning the density of the carrier particles are the same as those described above.

In one embodiment, the microcarrier particle may simultaneously satisfy two or more of the above-mentioned shape, porosity, density and/or size properties.

Other properties of the prepared particles are the same as described above.

In another embodiment, the present application can relate to a cell culture composition comprising the above-mentioned carrier particles and cells.

In this regard, the type of the cells is not particularly limited. For example, the cells contained in the culture composition may be adherent animal cells, specifically, cells such as fibroblasts, chondrocytes, mesenchymal stem cells, CHO, HEK 293, vero cells, BHK21 or MDCK.

The cell culture composition may further include a medium solution. The medium solution may contain nutrients close to the conditions of the living body based on body fluids such as plasma or lymph, and various additives for sufficiently satisfying environmental conditions such as pH, temperature, and osmotic pressure. As these additives, various materials widely known in the field of cell culture-related technology can be used without limitation.

In one embodiment, the microcarriers and cells may have a lower density than the medium solution. Specifically, according to one embodiment of the present application, the carrier particles may have a density within the range of 0.95 g/cm³ to 1.00 g/cm³, and the cells may have a density in the range of 1.10 to 1.25 g/cm³ (about 1.2 g/cm³). Accordingly, the low density carrier particles injected into the medium solution can float in the medium solution. As the number of cells adhering to the surface of the floating carrier particles gradually increases, the density of the microcarriers to which the cells adhere also gradually increases, and may sink to the bottom of the container containing the medium solution. And, after cell culture, the cultured cells can be secured by isolating the cells from the micro-carrier-cell complex through centrifugal separation.

In another embodiment, the present application can relate to a method for preparing a cell culture composition. The method for preparing the cell culture composition may include a step of mixing microcarrier particles, cells, and a medium solution.

Specifically, the method for preparing the cell culture composition may include a step of preparing the above-mentioned microcarrier particles; and a step of mixing the microcarrier particles, cells and media solution. At this time, the details concerning the microcarrier particles, cells, and medium solution is the same as those described above.

Advantageous Effects

According to the present application, micro-carriers that have a high degree of uniformity in shape or form, are porous, are advantageous for cell culture and centrifugal separation; and a composition including the same is provided.

BRIEF DESCRIPTION OF THE DRAWINGS

FIGS. 2(a) to 2(e) are each an SEM image of a part of the particles prepared in each of Comparative Examples 1 to 5. The white bar at the right-side lower end of each image means a size of 150 μm. In the case of Comparative Example 4, since particles of 1 mm or larger were obtained as in Table 2, the particles were not compared through the image in which 150 μm-sized white bars were shown.

Figure 1A:
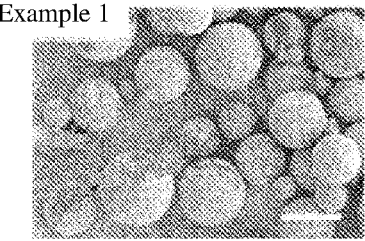
FIGS. 1(a) to 1(c) are each an SEM image of a part of the particles prepared in each of Examples 1 to 3. The white bar at the right-side lower end of each image means a size of 150 μm.
Figure 1B:
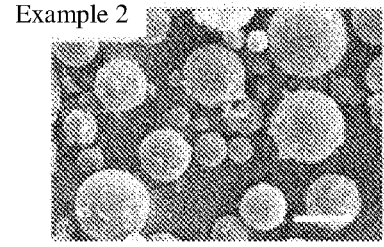
Figure 1C:
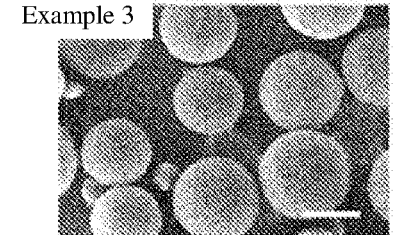
Figure 3A:
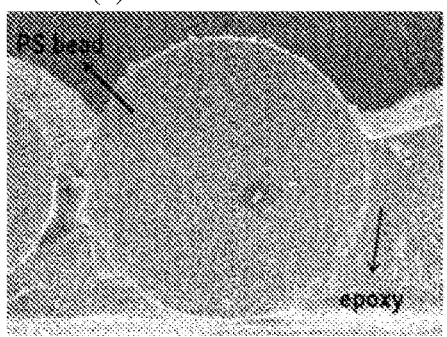
FIGS. 3(a) and 3(b) are each a view showing the internal structure of the particles prepared according to Example 1.
Figure 3B:
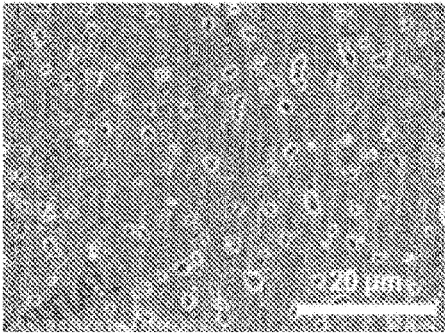

Specifically, it is confirmed that pores having a size of about 1 to 3 µm are formed inside the particles prepared according to Example 1.

Hereinafter, the action and effect of the invention will be described in more detail with reference to specific examples. However, these examples are for illustrative purposes only and are not intended to limit the scope of rights of the invention in any manner.

EXAMPLE AND COMPARATIVE EXAMPLE

Example 1

(1) Preparation of Dispersive Phase 8 g of a mixture of styrene monomer (st), divinylbezene (DVB) as a crosslinking agent and low-density hydrocarbon oil (density in the range of 0.750 to 0.800 $g/cm^3$) in the content ratio shown in Table 1 below was stirred in a 100 ml vial. After that, benzoyl peroxide (BPO) and tert-butyl peroxybenzoate (t-BP), which are thermal initiators, were additionally added to a vial, and the mixture was stirred at normal temperature for about 5 minutes. The content between each component is shown in Table 1 below.

(2) Preparation of Continuous Phase 2.5 g of PVA having a weight average molecular weight in the range of 85,000 to 125,000 and a hydrolysis rate of 87 to 89% was dissolved in 250 g of distilled water. The detailed contents are shown in Table 1.

(3) Preparation of Particles by Suspension Polymerization 50 g of 1% PVA aqueous solution was mixed with the dispersive phase and stirred in an oil bath until a homogeneous dispersion was obtained. Specifically, the oil bath was gradually heated at normal temperature while stirring at 800 rpm, and suspension polymerization was performed under the conditions of a temperature of 85 to 88° C. and a speed of 600 to 800 rpm. The polymerization was carried out under nitrogen purging.

(4) Obtaining Particles

After 6 hours of reaction, the prepared particles were recovered through a 100 µm sieve, and washed 5 times with ethanol, and then dried at normal temperature.

Examples 2 to 3 and Comparative Examples 1 to 5

Particles were obtained through the same process as in Example 1, except that the composition of the dispersive phase and the continuous phase were adjusted as shown in Table 1 below.

Measuring Method (1) Surface Tension of Continuous Phase (unit: mN/m)

The surface tension was measured according to a ring method. Specifically, the surface tension was measured at normal temperature using a platinum ring and a surface tension meter (Surface Electro Optics).

(2) Viscosity of Continuous Phase (unit: cp)

The viscosity was measured according to a shear rate. Specifically, the viscosity was measured using an LVDV2T instrument (Brookfield), which is a rotational viscometer, under the conditions of a shear rate range of 66 to 264 l/s and normal temperature (about 25° C.).

(3) Weight Average Molecular Weight

The weight average molecular weight (in terms of standard polystyrene) of PVA (or PVP) was measured using gel permeation chromatography (GPC).

(4) Hydrolyzed Degree

The hydrolyzed degree of the measured PVA was measured using 1H-NMR. For reference, as the hydrolysis proceeds, the hydrogen peak (H peak) at ethylene decreases, and the hydrogen peak at the hydroxyl group increases.

(5) Oil/Water Fraction

When the dispersive phase is regarded as the oil phase and the continuous phase is regarded as the water phase, it means the ratio of the weight ($W_B$) of the dispersive phase relative to the weight ($W_A$) of the continuous phase.

TABLE 1

| | Example 1 | Example 2 | Example 3 | Comparative Example 1 | Comparative Example 2 | Comparative Example 3 | Comparative Example 4 | Comparative Example 5 |
|---|---|---|---|---|---|---|---|---|
| Oil/Water fraction (WB/WA) | 0.20 | 0.15 | 0.14 | 0.10 | 0.10 | 0.15 | 0.15 | 0.15 |
| | | | | Dispersive phase | | | | |
| St:DVB (weight ratio)[1] | 1:0.33 | 1:0.33 | 1:0.33 | 1:0.33 | 1:0.33 | 1:0.33 | 1:0.33 | 1:0.33 |
| Oil content (wt %)[2] | 20 | 20 | 20 | 20 | 20 | 20 | 20 | 20 |
| BPO content (wt %)[3] | 2.06 | 2.06 | 2.06 | 2.06 | 2.06 | 2.06 | 2.06 | 2.06 |
| t-BP content (wt %)[4] | 0.3 | 0.3 | 0.3 | 0.3 | 0.3 | 0.3 | 0.3 | 0.3 |
| | | | | Continuous phase | | | | |
| Water content (g) | 50 | 50 | 50 | 50 | 50 | 50 | 50 | 50 |
| Concentration (%) of PVA(or PVP)[5] | PVA 1.01% | PVA 2% | PVA 2% (1% + 1%[6]) | PVA 0.6% | PVA 0.8% | PVA 1.01% | PVP 1.01% | PVP 1.01% |
| Molecular weight/ hydrolyzed degree of PVA(or PVP) | | | [7] | | | [8] | [9] | [10] |
| Surface energy | 54 | 54 | 50 | 55 | 54.5 | 49 | 65 | 66 |
| Viscosity (cp) | ≥2.0 | 4.0 | 4.0 | ≤1 | ≤1.5 | 1.6 | 1.5 | 3.0 |

In Table 1, the reference numerals 1) to 10) are as follows.
1) Ratio of the weight ratio of St (styrene) to the weight of DVB (divinylbenzene)
2) Weight % occupied by the oil when the weight of the entire composition of the dispersive phase is 100,
3) Weight % occupied by BPO when the weight of the entire composition of the dispersive phase is 100,
4) Weight % occupied by t-BP when the weight of the entire composition of the dispersive phase is 100,
5) Weight % occupied by PVA (polyvinyl alcohol) or PVP (polyvinyl pyrrolidone) when the weight of the entire composition of the continuous phase is 100,
6) PVA is added to the continuous phase at a concentration of 1%, and a continuous phase composition having a concentration of PVA of 1% is additionally added during progress of suspension polymerization (a point of time when the polymerization rate is about 10%)
7) Use of PVA that satisfies the weight average molecular weight in the range of 85,000 to 125,000 and the hydrolyzed degree in the range of 87 to 89%
8) Use of PVA that satisfies the weight average molecular weight in the range of 13,000 to 50,000 and the hydrolyzed degree in the range of 87 to 89%
9) Use of PVP having a weight average molecular weight of about 55,000
10) Use of PVP having a weight average molecular weight of about 360,000

Results of Experiments of Suspension Polymerization Product

The items shown in Table 2 were measured for the particles obtained in Examples and Comparative Examples. The measurement method for each item is as follows.

1. Recovery Rate of Particles (%)

In Examples, the ratio of the solid content (recovered polystyrene particles) to the substances (styrene and divinylbenzene) that actually participated in the polymerization of polystyrene particles was calculated according to Equation 3 below.

$$\{(\text{Weight of Recovered Polystyrene Particles(g)})/(\text{Weight of Styrene and Divinylbenzene(g)})\} \times 100 \qquad \text{[Equation 3]}$$

The recovery rate of the particles is related to the stability of the dispersive phase in the suspension polymerization reaction system. Specifically, when the stability of the dispersive phase is ensured, the dispersive phase is not cracked during polymerization and can be polymerized into particles. Such stability may vary depending on the components forming the dispersive phase and the continuous phase and whether the conditions 1 and 2 are satisfied.

2. Confirmation of Particle Density (g/cm$^3$)

Under the conditions of normal temperature (about 25° C.) and atmospheric pressure (1 atm), carrier particles obtained in Examples and Comparative Examples were added to an aqueous ethanol solution having a density of 0.95 g/cm$^3$ and an aqueous ethanol solution having a density of 0.99 g/cm$^3$, respectively. Then, it was confirmed whether the carrier particles floated or settled, and then the density was evaluated based on the following criteria. The density of the particles can be determined according to the presence or absence of the use of hydrocarbon oil, its content, and the residual of the hydrocarbon oil in the dispersive phase due to the satisfaction of the conditions 1 and 2.
1) floats in an aqueous ethanol solution with a density of 0.95 g/cm$^3$: the density of the carrier is less than 0.95 g/cm$^3$.

2) settles in an aqueous ethanol solution with a density of 0.99 g/cm$^3$: the density of the carrier exceeds 0.99 g/cm$^3$.
3) settles in an aqueous ethanol solution with a density of 0.95 g/cm$^3$ and floats in an aqueous ethanol solution with a density of 0.99 g/cm$^3$: the density of the carrier is 0.95 g/cm$^3$ or more and 0.99 g/cm$^3$ or less.

3. Particle Size

The microcarrier particles obtained in Examples and Comparative Examples were prepared, and then the particle diameters of 100 particles were measured through an optical microscope. The arithmetic mean value of the measured diameters was calculated. Specifically, the diameters of individual particles was calculated by calculating the two-dimensional (2D) plane area of the particles through an optical microscope and then back calculating Equation ($S=\pi r^2$) for the plane area.

The surface tension of the continuous phase affects the interfacial tension between the dispersive phase and the continuous phase and the shape or size of the dispersive phase. The surface tension under the condition 1 described above can prevent cracking of the dispersive phase or excessive decrease or increase in the size of the dispersive phase. In addition, the viscosity of the continuous phase affects the movement of the dispersive phase upon stirring associated with suspension polymerization. Appropriate levels of viscosity, such as the condition 2 described above reduces collisions and cracks between droplets or particles, and it also has a positive effect on the shape of the particles (flatness or single-shaped particles).

4. Percentage of Single-Shaped Particles

The microcarrier particles obtained in Examples and Comparative Examples were prepared, scanning electron microscopy (SEM) images were photographed (using a magnification of ×250). A plurality of images, in which 30 or more particles were visually confirmed from the photographed image, were randomly selected, and the ratio of the number of single-shaped particles without satellite particles on the surface to the total number of the particles observed in each image was calculated.

The proportion of single-shaped particles being high is associated with less aggregation of particles due to particle collision during suspension polymerization. In particular, a viscosity of the condition 2 of the continuous phase 2 relates to the movement of the dispersive phase particles.

In the case of having a viscosity that satisfies the condition 2, the movement of the dispersive phase particles is reduced, particle aggregation and agglomeration due to particle collisions are reduced, and the proportion of single-shaped particles can be increased. At this time, when the condition 1 is satisfied, excessive decrease in particle size due to low surface tension and decrease in interfacial tension caused thereby is suppressed. Therefore, when the condition 1 and the condition 2 are satisfied, the proportion of single-shaped particles having an appropriate size can be increased.

5. Internal Structure of Particles

For the cell culture microcarrier obtained in Example 1, the internal structure of the particles was confirmed through SEM. Specifically, after embedding the particles into the epoxy, the cross section was prepared through ion milling, and the shape of the particle cross section was confirmed through SEM.

TABLE 2

| | Example 1 | Example 2 | Example 3 | Comparative Example 1 | Comparative Example 2 | Comparative Example 3 | Comparative Example 4 | Comparative Example 5 |
|---|---|---|---|---|---|---|---|---|
| Particle recovery rate (%) | 75.3 | 74.2 | 88.0 | 48.5 | 50.0 | 66.8 | N.A. | 94.8 |
| Particle density (g/cm³) | within the range of 0.95-0.99 | within the range of 0.95-0.99 | within the range of 0.95-0.99 | within the range of 0.95-0.99 | within the range of 0.95-0.99 | within the range of 0.95-0.99 | N.A. | within the range of 0.95-0.99 |
| Particle size (μm)(based on single particle shape) | 130 ± 33 | 197 ± 28 | 182 ± 27 | 115 ± 16 | 114 ± 16 | 84 ± 16 | 1 mm or more | less than 100 μm, more than 300 μm |
| Proportion of single-shaped particles (%) | 93.55 | 80.65 | 100.0 | 86.11 | 93.55 | 69.49 | 87.69 | 80.65 |

Comparing Comparative Examples 1 to 3 with Examples through Table 1 and Table 2, it can be seen that the particle recovery rate of Examples according to the present application is superior to that of Comparative Examples. This means that the method of the present application induces the formation and polymerization of a stable dispersed phase, and as a result, a large amount of carrier particles having low density and large surface area properties can be improved. (process efficiency or yield is improved).

In addition, comparing Comparative Examples 4 and 5 with Examples through Tables 1 and 2, it can be seen that the Examples according to the present application provide micro-sized particles with a narrow particle size distribution and an appropriate size as compared with Comparative Examples 4 and 5. Further, it is confirmed that in the case of Examples, the proportion of single-shaped particles (of appropriate size) is generally higher than in Comparative Examples 4 and 5. This means that the method of the present application can provide a large surface area suitable for cell culture.

Moreover, comparing Comparative Examples 4 and 5 with Examples, it can be seen that in the case of using PVP, the particle size of the particles prepared by suspension polymerization becomes excessively large or the particle size distribution becomes excessively wide. The weight of the particles is taken into account when calculating the recovery rate, and the recovery rate of Comparative Example 5 being high is because the weight of the large particles (size of more than 300 μm) prepared in Comparative Example 5 is relatively large. On the other hand, the molecular weight of the PVP used in Comparative Example 4 is very small compared to the molecular weight of the PVP used in Comparative Example 5, whereby in Comparative Example 4, the steric effect between PVPs was weak, and aggregation between particles was excessively occurred, so that the size of the particles was very large, and it was difficult to confirm the individual particle density or the recovery rate.

In summary, the present application can provide porous carrier particles having a single shape, spherical shape, low density properties and excellent flatness with a high recovery rate.

The invention claimed is:

1. A method for preparing microcarrier particles for cell culture, the method comprising the steps of:
mixing a continuous phase composition (A) satisfying the following conditions 1 and 2; and a dispersive phase composition (B) containing a polymerizable monomer (b1) and then performing suspension polymerization,
wherein the dispersive phase composition (B) comprises a hydrocarbon oil (b3) in an amount of 10 to 20% by weight based on the total content of the dispersive phase composition, wherein the microcarrier particles include microcarrier particles having a density in the range of 0.95 g/cm³ to 1.00 g/cm³:

$$45 \text{ mN/m} < \text{Surface Tension of Continuous Phase Composition} \leq 54 \text{ mN/m} \quad \text{[Condition 1]}$$

$$\text{Viscosity of Continuous Phase Composition} \geq 2.0 \text{ cp, and} \quad \text{[Condition 2]}$$

wherein, in the [Condition 1], the surface tension is measured at a normal temperature according to a ring method, and in the [Condition 2], the viscosity is measured under conditions of a shear rate in the range of 66 to 264 l/s and a normal temperature.

2. The method for preparing microcarrier particles for cell culture according to claim 1, wherein the continuous phase composition (A) comprises water and poly(vinyl alcohol) (PVA).

3. The method for preparing microcarrier particles for cell culture according to claim 2, wherein the polyvinyl alcohol (PVA) has a weight average molecular weight in the range of 80,000 to 190,000 and a hydrolyzed degree in the range of 80 to 99%.

4. The method for preparing microcarrier particles for cell culture according to claim 2, wherein the continuous phase composition (A) contains at least 1.0% by weight of the polyvinyl alcohol based on the total weight of the continuous phase composition.

5. The method for preparing microcarrier particles for cell culture according to claim 1, wherein the dispersive phase composition (B) comprises a styrene monomer as the polymerizable monomer (b1).

6. The method for preparing microcarrier particles for cell culture according to claim 5, wherein the dispersive phase composition (B) further comprises a crosslinking agent (b2).

7. The method for preparing microcarrier particles for cell culture according to claim 6, wherein the dispersive phase composition (B) contains the crosslinking agent in an amount of 3 to 300 parts by weight based on 100 parts by weight of the styrene monomer.

8. The method for preparing microcarrier particles for cell culture according to claim 1, wherein the hydrocarbon oil has a density in the range of 0.750 g/cm$^3$ to 0.800 g/cm$^3$.

9. The method for preparing microcarrier particles for cell culture according to claim 1, wherein the hydrocarbon oil contains a linear or branched saturated hydrocarbon compound having 12 to 50 carbon atoms.

10. The method for preparing microcarrier particles for cell culture according to claim 1, wherein the suspension polymerization is performed under conditions of a temperature of 80 to 95° C. and at a speed of 300 to 900 rpm.

11. The method for preparing microcarrier particles for cell culture according to claim 1, wherein the step of mixing the continuous phase composition (A) and the dispersive phase composition (B) followed by applying a shearing force to homogenize the dispersive phase composition (B) in the continuous phase composition (A) in the form of droplets; and the dispersive phase composition (B) is subjected to the suspension polymerization.

12. The method for preparing microcarrier particles for cell culture according to claim 1, further comprising a step of adding an additional amount of the continuous phase composition (A) during the suspension polymerization when the polymerization rate related to the suspension polymerization is in the range of at least 5% to 70%.

13. The method for preparing microcarrier particles for cell culture according to claim 1, wherein at least 80% of the microcarrier particles have a single shape where satellite particles are not present on the surface of the particles.

14. The method for preparing microcarrier particles for cell culture according to claim 1, wherein the microcarrier particles include porous microcarrier particles that are spherical and have pores of 5 μm or less.

15. The method for preparing microcarrier particles for cell culture according to claim 1, wherein the microcarrier particles include microcarrier particles having a diameter in the range of 90 to 250 μm.

\* \* \* \* \*